United States Patent
Murray et al.

(10) Patent No.: US 10,791,962 B2
(45) Date of Patent: Oct. 6, 2020

(54) INSULATING A PROTECTIVE COVER FOR A SEAL TO SENSOR ASSOCIATED WITH A SPACESUIT

(71) Applicant: HAMILTON SUNDSTRAND CORPORATION, Charlotte, NC (US)

(72) Inventors: Sean K. Murray, Enfield, CT (US); Robert G. Avalone, Middletown, CT (US); Gregory John Quinn, Windsor, CT (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 744 days.

(21) Appl. No.: 15/415,993

(22) Filed: Jan. 26, 2017

(65) Prior Publication Data

US 2018/0206765 A1    Jul. 26, 2018

(51) Int. Cl.
```
A61B 5/097      (2006.01)
G01N 33/00      (2006.01)
B64G 6/00       (2006.01)
G01N 21/3504    (2014.01)
A61B 5/08       (2006.01)
```
(52) U.S. Cl.
CPC .............. *A61B 5/097* (2013.01); *A61B 5/082* (2013.01); *B64G 6/00* (2013.01); *G01N 21/3504* (2013.01); *G01N 33/004* (2013.01); *G01N 2201/021* (2013.01); *G01N 2201/0231* (2013.01)

(58) Field of Classification Search
CPC ......... G01N 21/3504; G01N 2201/021; G01N 2201/0231; G01N 33/004; B64G 6/00; A61B 5/082; A61B 5/097
See application file for complete search history.

(56) References Cited

U.S. PATENT DOCUMENTS

| | | | | |
|---|---|---|---|---|
| 4,095,593 | A * | 6/1978 | Webbon | B64G 6/00 128/202.11 |
| 5,742,200 | A * | 4/1998 | He | G01J 1/44 327/17 |
| 6,312,389 | B1 * | 11/2001 | Kofoed | A61B 5/083 600/532 |
| 6,325,978 | B1 * | 12/2001 | Labuda | A61B 5/0833 422/84 |
| 7,341,563 | B2 * | 3/2008 | Rich | A61B 5/097 600/532 |
| 7,658,891 | B1 | 2/2010 | Barnes | |
| 9,295,410 | B2 * | 3/2016 | Weckstrom | A61B 5/0833 |
| 2002/0029003 | A1 * | 3/2002 | Mace | A61B 5/083 600/532 |

(Continued)

FOREIGN PATENT DOCUMENTS

| | | |
|---|---|---|
| KR | 101349965 B1 | 1/2014 |
| WO | 2014143175 A1 | 9/2014 |

*Primary Examiner* — Natalie Huls

(74) *Attorney, Agent, or Firm* — Carlson, Gaskey & Olds, P.C.

(57) ABSTRACT

A carbon dioxide sensor has a conduit connecting to a source of breathing air and delivering a sample of breathing air into a test chamber. A radiation source applies radiation across the chamber. A sensor detects modification in the radiation as it passes through the air sample in the test chamber and communicates with electronics to identify a percentage of carbon dioxide in the sample. A rigid cover surrounds the radiation source, the test chamber, and the sensor. A spacesuit is also disclosed.

16 Claims, 2 Drawing Sheets

(56) References Cited

U.S. PATENT DOCUMENTS

| | | | |
|---|---|---|---|
| 2004/0055067 A1* | 3/2004 | Boettcher | A62B 17/001 2/2.13 |
| 2010/0147699 A1* | 6/2010 | Wachsman | B01D 53/32 205/634 |
| 2010/0249631 A1* | 9/2010 | Aoki | A61B 5/0836 600/532 |
| 2014/0320312 A1* | 10/2014 | Sager | H04Q 9/00 340/870.16 |
| 2017/0242149 A1* | 8/2017 | Fujisawa | G01N 21/3504 |
| 2019/0339196 A1* | 11/2019 | Abel | G01N 33/004 |

\* cited by examiner

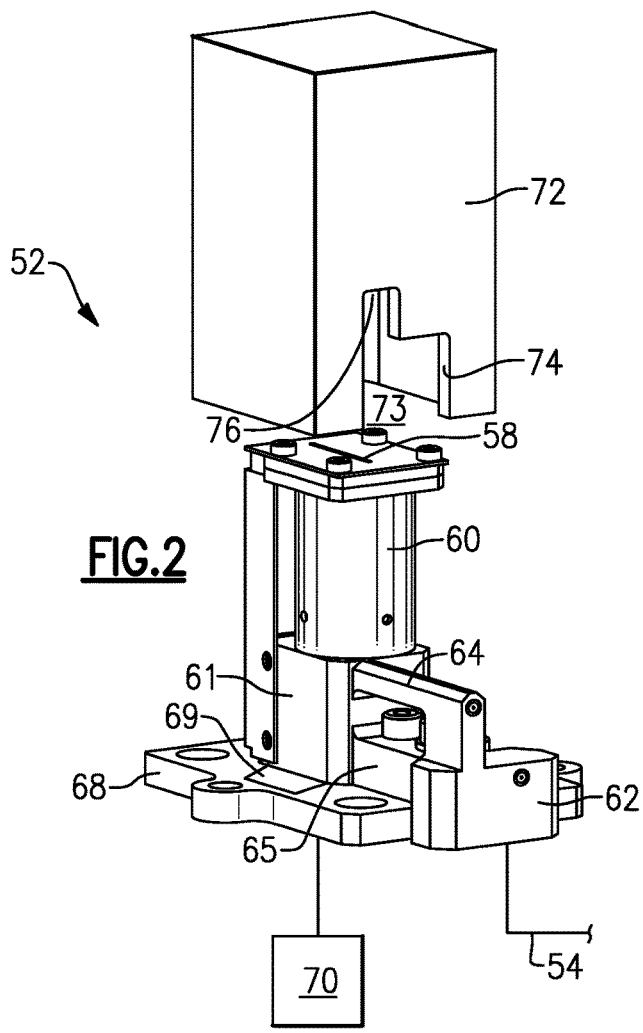
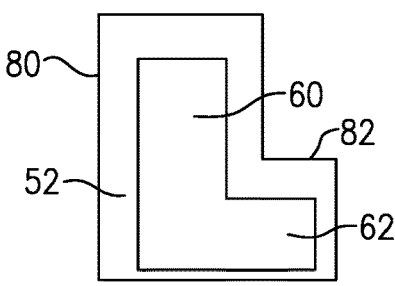
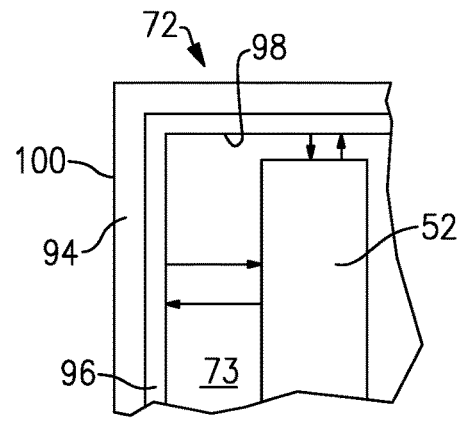
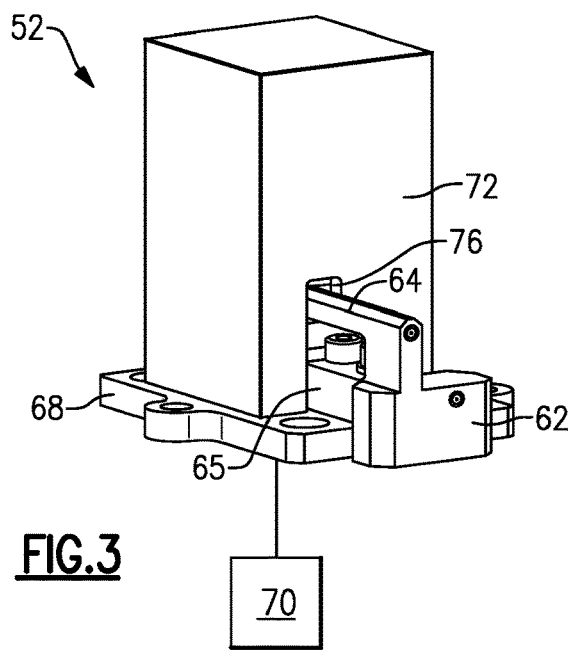

INSULATING A PROTECTIVE COVER FOR A SEAL TO SENSOR ASSOCIATED WITH A SPACESUIT

BACKGROUND OF THE INVENTION

This application relates to a cover to protect and insulate components of a carbon dioxide ($CO_2$) sensor that is to be utilized in space applications.

As can be appreciated, space applications can provide a harsh environment for electronic components. Astronauts are frequently called upon to leave space vehicles in a spacesuit. During such journeys, they are provided with a supply of breathing air.

It is known to include a $CO_2$ sensor to detect the level of $CO_2$ in the astronaut's breathing air. The sensor may utilize an infrared detecting scheme which passes infrared light through a sample of air. Sensors detect and analyze a percentage of $CO_2$ in the air sample.

It has been proposed to package these sensors on the outside of a spacesuit. Thus, the sensor must operate in harsh conditions.

SUMMARY OF THE INVENTION

A carbon dioxide sensor has a conduit connecting to a source of breathing air and delivering a sample of breathing air into a test chamber. A radiation source applies radiation across the chamber. A sensor detects modification in the radiation as it passes through the air sample in the test chamber and communicates with electronics to identify a percentage of carbon dioxide in the sample. A rigid cover surrounds the radiation source, the test chamber, and the sensor.

A spacesuit is also disclosed.

These and other features may be best understood from the following drawings and specification.

BRIEF DESCRIPTION OF THE DRAWINGS

FIG. 2 is an exploded view of a sensor and cover.
FIG. 3 is an assembly view.
FIG. 4 shows an alternative embodiment.
FIG. 5 shows a feature.

DETAILED DESCRIPTION

Figure 1:
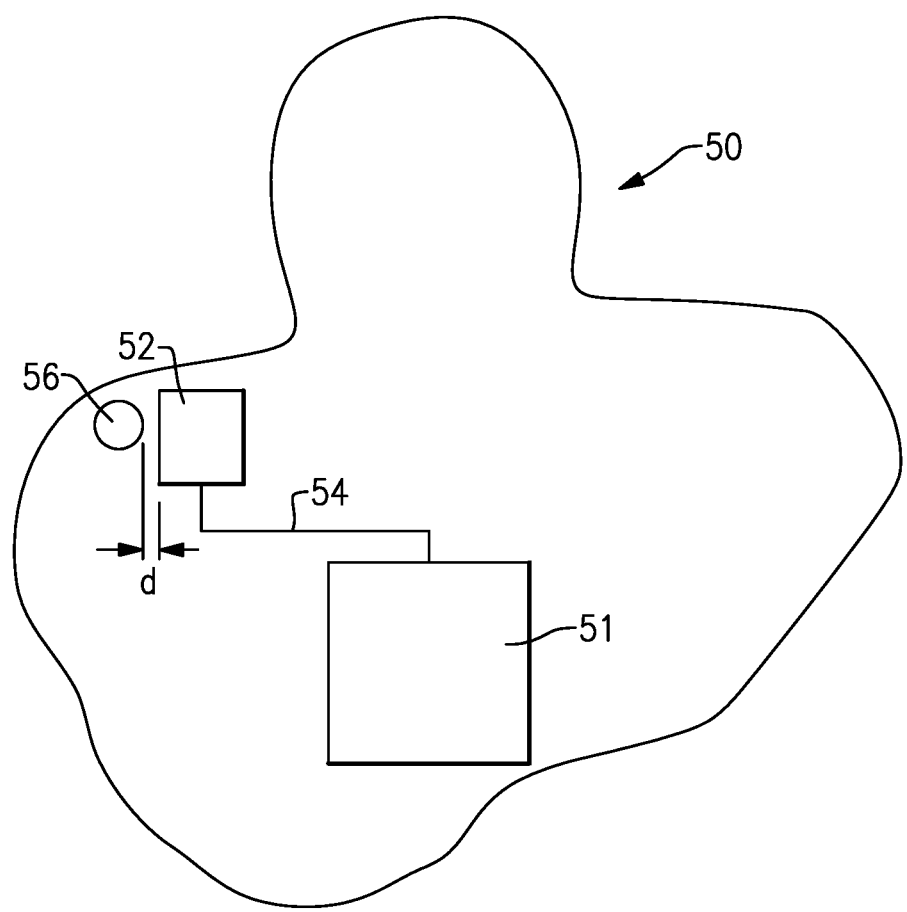
FIG. 1 schematically shows a spacesuit.

A spacesuit 50 is illustrated schematically in FIG. 1. As known, a supply of breathing air 51 is utilized by the astronaut wearing the spacesuit 50.

The astronaut may leave a space vehicle for relatively prolonged amounts of time and the breathing air supply 51 must be monitored to ensure that it is providing adequate oxygen flow to the astronaut. Thus, a $CO_2$ sensor 52 is associated with an outside area on the spacesuit 50. In one proposal, it is positioned near a shoulder of the astronaut and on a rear side of the spacesuit 50.

A sample supply line 54 connects the breathing air supply 51 to the sensor 52. As will be disclosed below, the sensor 52 includes a number of components which are sensitive to mechanical damage. In addition, undue moisture on the internal sensor components can affect their operation. Further, exposure to temperature extremes can also impact upon the operation of the sensor.

Further, when operating outside of the space station or a crewed spacecraft, as examples, the wearer will experience earth orbits frequently. Thus, the environment outside of the suit is exposed to extreme temperature changes such as when the wearer is exposed to the sun and when the wearer is on an opposed side of the earth and exposed only to the darkness of space. As can be appreciated, there could be an extreme temperature gradient between those two positions.

In addition, the design of the spacesuit includes a port 56 for expelling water which may have generated inside of the spacesuit 50 for various reasons. This port typically includes a hole in the outer thermal insulation of the space suit. Since the sensor 52 within the suit 50, is shown located somewhat near this port, it potentially has a radiative view factor to space, exposing it to extreme temperatures. When the sensor is exposed to extreme cold environments, water vapor within the breathing gas sample may condense to form liquid water. The internal sensor components may be adversely affected by the presence of liquid water.

As illustrated, the port 56 is open to an area outwardly of the suit 50. Thus, the port 56 allows communication of the high and low temperature fluctuations within the suit, and into an area receiving sensor 52. As shown, an outer portion of the port 56 is within a small distance d from the closest portion of the sensor 52. As such, the sensor 52 is effectively exposed to those same temperature fluctuations. In one embodiment, a hydraulic diameter D of the port 56 may be on the order of 2", while the distance d could be less than 1". In embodiments, the hydraulic diameter D of the port is more than twice the distance d.

As disclosed, the sensor 52 is provided with a protective and insulating cover which will protect the sensitive internal components from mechanical damage. Further, by isolating the components within an enclosure of the cover, the components will be protected from extreme temperature gradients and also exposure to liquid water as described above.

As shown in FIG. 2, the air supply line 54 leads to a manifold 62, an air supply tube 64, and an air return tube 65. The air supply from conduit 64 passes into a test cylinder 60 that is generally cylindrical and a second test chamber 61.

An infrared or other radiation source 58 is provided at an outer end of the chamber portion 60. A $CO_2$ sensor 69 is provided within a base 68. Both source 58 and sensor 69 are shown schematically.

The sensor 69 communicates with electronics 70, shown schematically.

A rigid cover 72 is shown having an internal space 73 and an opening 74 and 76. Internal space can be seen to be generally rectangular in cross-section. Opening 76 extends outwardly further than the opening portion 74, while opening portion 74 has a greater width than portion 76.

The opening in the housing has a smaller portion and a larger portion. The larger portion receives the air return tube.

As shown in FIG. 3, with cover 72 placed on the sensor 52, the conduit 64 and return tube 65 extend outwardly through the opening portion 74 and 76.

The cover 72 insulates the components such as the sensor 69 and infrared source 58 along with any associated wire, thermistors, and the electronics 70. The repeated exposure to sun/darkness will no longer provide temperature change challenges to the sensitive components. In addition, moisture will also no longer be able to condense within those components. Of course, the rigid cover 72 also provides protection from mechanical impact. The internal space 73 preferentially has a surface reflective to infrared composed of highly polished metal such as aluminum, nickel or gold.

FIG. 4 shows an alternative embodiment cover 80. Cover 80 has a portion 82 which also encloses the connection structure 62 on the sensor 52.

FIG. 5 shows another feature of cover 72 (or 80). The sensor 52 is shown received within the space 73. The cover is shown to have an outer layer 94 and an inner layer 96. An inner surface 98 of the layer 96 is more reflective to infrared radiation than is the outer surface 100 of the layer 94. While two layers are shown, the same relationship between the inner and outer surfaces 98/100, and their respective reflective properties could be provided with a single layer cover. The inner surface may be provided by a metallic coating, and may be highly polished metal. Example metals could be aluminum, nickel or gold.

As shown in FIG. 5, now, when heat is generated by the sensor 52, that heat is reflected back from the reflective surface 98 such that it heats the sensor 52, rather than being dissipated away as might be the case if there was no cover.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A carbon dioxide sensor comprising:
    a conduit connecting to a source of breathing air and delivering a sample of breathing air into a test chamber;
    a radiation source for applying radiation across said chamber and a sensor for detecting modification in the radiation as it passes through the air sample in the test chamber and communicating with electronics to identify a percentage of carbon dioxide in the sample; and
    a rigid cover surrounding said radiation source, said test chamber, and said sensor; and
    wherein said cover has a first portion surrounding said radiation source, said test chamber and said sensor, and a second portion that encloses a connection point for said conduit to be connected to the source of breathing air.

2. The carbon dioxide sensor as set forth in claim 1, wherein said radiation source is an infrared source.

3. The carbon dioxide sensor as set forth in claim 1, wherein an inner surface of said cover facing said sensor has greater reflectivity to infrared radiation than does an outer surface of said cover.

4. The carbon dioxide sensor as set forth in claim 3, wherein said outer surface of said cover is formed by a first material and said inner surface of said cover is formed by a second material.

5. The carbon dioxide sensor as set forth in claim 4, wherein said inner surface is provided by a polished metal.

6. The carbon dioxide sensor as set forth in claim 3, wherein said inner surface is one of nickel, aluminum, or gold.

7. The carbon dioxide sensor as set forth in claim 3, wherein said inner surface is provided by a polished metal.

8. A spacesuit comprising:
    a suit;
    a source of breathing air and a conduit delivering a sample of the breathing air into a test chamber of a $CO_2$ sensor;
    said CO2 sensor being within said suit, said CO2 sensor also including a radiation source for applying radiation across said chamber and a sensor for detecting modification in the radiation as it passes through the air sample in the test chamber and communicating with electronics to identify a particular percentage of carbon dioxide in the sample;
    a rigid cover surrounding said radiation source, said test chamber, and said sensor;
    wherein there is a port adjacent to said carbon dioxide sensor for expelling fluid from within said spacesuit; and
    wherein said port has a hydraulic diameter, and a distance between an outer edge of said port, and a closest portion of said carbon dioxide sensor is less than said hydraulic diameter.

9. The spacesuit as set forth in claim 8, wherein said radiation source is an infrared source.

10. The spacesuit as set forth in claim 9, wherein an inner surface of said cover facing said sensor has greater reflectivity to infrared radiation than does an outer surface of said cover.

11. The spacesuit as set forth in claim 10, wherein said inner surface is provided by a polished metal.

12. The spacesuit as set forth in claim 8, wherein an inner surface of said cover facing said sensor has greater reflectivity to infrared radiation than does an outer surface of said cover.

13. The spacesuit as set forth in claim 12, wherein said outer surface of said cover is formed by a first material and said inner surface of said cover is formed by a second material.

14. The spacesuit as set forth in claim 13, wherein said inner surface is provided by a polished metal.

15. The spacesuit as set forth in claim 12, wherein said inner surface is one of nickel, aluminum, or gold.

16. The spacesuit as set forth in claim 12, wherein said inner surface is provided by a polished metal.

* * * * *